United States Patent [19]
Chester

[11] Patent Number: 4,687,734
[45] Date of Patent: Aug. 18, 1987

[54] IMMUNOASSAY FOR THE DETECTION OF HUMAN COLON CANCER USING A POLYCLONAL ANTIBODY DERIVED FROM A CAPILLARY CULTURE OF TUMOR CELLS

[76] Inventor: Samuel J. Chester, 56 Dellwood Rd., Cranston, R.I. 02920

[21] Appl. No.: 618,085

[22] Filed: Jun. 7, 1984

[51] Int. Cl.⁴ ............................................. G01N 33/53
[52] U.S. Cl. ........................................ 435/7; 436/501; 436/503; 436/506; 436/507; 436/536; 436/542; 436/544; 436/545; 436/547; 436/804; 436/808; 436/813; 436/821; 436/824; 436/825; 436/828
[58] Field of Search ............... 436/501, 503, 506, 507, 436/536, 542, 544, 545, 547, 804, 808, 813, 821, 824, 825, 828; 435/7

[56] References Cited

U.S. PATENT DOCUMENTS

| | | | |
|---|---|---|---|
| 4,241,044 | 12/1980 | Kim | 436/518 |
| 4,342,566 | 8/1982 | Theofilopoulos et al. | 436/507 |
| 4,459,359 | 7/1984 | Neurath | 436/531 |
| 4,472,371 | 9/1984 | Burchiel | 424/1.1 |
| 4,495,295 | 1/1985 | Neurath | 436/531 |
| 4,514,506 | 4/1985 | Braatz et al. | 436/531 |

OTHER PUBLICATIONS

Ravikumar et al, Cancer, 53(6), 1984, 1373–78.
Terman et al, FEBS Letters, 68(1), 1976, 89–94.

*Primary Examiner*—Christine M. Nucker
*Attorney, Agent, or Firm*—Charles Hieken

[57] ABSTRACT

A procedure for detecting malignancy includes culturing human colon tumor cells in a capillary system. A rabbit is immunized with byproducts of the culture. An antibody produced in the rabbit is labeled with $^{125}I$ using lactoperoxidase according to a known method. Blood samples are drawn from a being to be tested. The drawn blood is processed to produce serum. The immune complexes are removed from the serum with purified protein A from the Staphlococcus Aureus Cowan strain. The removed immunocomplexes are dissociated with 0.2M glycene/HCl pH 2.8. The labeled antibody is combined with the antigen component of the immunocomplex to produce a new labeled immunocomplex. The newly formed immunocomplex is precipitated with PEG 6000. The newly formed labeled immunocomplexes are counted in a gamma auto counter.

3 Claims, No Drawings

IMMUNOASSAY FOR THE DETECTION OF HUMAN COLON CANCER USING A POLYCLONAL ANTIBODY DERIVED FROM A CAPILLARY CULTURE OF TUMOR CELLS

The present invention relates in general to the early detection of human colon cancer and more particularly concerns novel combinations of materials and techniques for the early detection of human colon cancer before clinically evident and thereby facilitate early treatment to enhance survival with reduced physical impairment.

During normal immune responses immune complexes (IC) are formed when antibodies combine with their corresponding antigens, which may be tissue fixed or free in serum and other body fluids.

The possible pathogenic role of IC in diseases of man and their mode of action have been studied with the refinement of the necessary techniques as discussed in Dixon, F. J. (1963), The role antigen-antibody complexes in disease. The Harvey Lectures, 58:21–52. Soluble circulating IC (CIC) are important in chronic diseases such as cancer where there is a continuous production and release of antigenic materials as discussed in Theofilopoulos, A. N., Andrews, B. S., Urist, M. M., Morton, D. L., and Dixon, F. J. 1977, The nature of immune complexes in human cancer sera. J. Immunol. 119:657. Early detection of cancer, coupled with treatment, is essential in order to achieve better survival rates.

Because of the important role of IC in disease, the development of specific, sensitive, and reliable techniques for their demonstration in serum is desirable. The prior art includes three complement-dependent and two complement-independent methods available as described in Brown, C. A., Hall, C. L., Long. J. C. Carey, K., Weitzman, S. A., and Ainsenberg, A. G., Circulating immune complexes in Hodgkin's disease. Amer. J. Med., 64, 289–294 (1978); Brandeis, W. E., Helson, L., Wang, Y., Good, R. A., and Day, N. K., Circulating immune complexes in sera of children with neuroblastoma: correlation with stage of disease. J., Clin. Invest., 62, 1201–1209 (1978); Samayoa, E. A., McDuffie, F. C., Nelson, A. M., Go, V. L. W., Luthra, H. S., and Brumfield, H. W. 1977. Immunoglobulin complexes in sera of patients with malignancy. Int. J. Cancer 19:12; Kano, K., Nishimaki, T., Palosua, T., Loza, U., and Milgrom, F., Detection of circulating immune complexes by the inhibition of antiantibody. Clin. Immunol. Immunopath., 9, 425–435 (1978).

It is an important object of the invention to improve malignant colon cell detection.

According to the invention an assay deals with a specific labeled antibody against the dissociated antigen component of the CIC. In a specific form of the invention, detection of elevated levels of soluble CIC present in the serum of cancer patients provides an indication of the existence of certain colon tumors.

Numerous other features, objects and advantages of the invention will become apparent from the following specific examples.

Serum samples were obtained from normal individuals and patients who had histologically confirmed cancer of the colon, pancreas, lung and breast. All sera aliquoted into 0.750 ml samples, were stored frozen at −70° C. and thawed only once immediately before use.

In order to develop an antiserum against human colon tumor associated products, a cell suspension of human colon tumor cells was cultured in a commercially available Amicon capillary system. This system allowed the tumor cells to stay viable within an enclosed area, releasing molecules through a membrane wall into the media. One ml extra capillary samples (ECS), possibly containing shed tumor antigens and cell by-products, were removed daily and pooled at the end of two weeks. To immunize a rabbit a 1:10 dilution of this solution designated ECS/colon was given intramuscularly weekly for 10 weeks. Seven days after the last immunization, the rabbit was bled.

Because of species differences the rabbit produced antibodies directed against normal human serum components and other proteins not related to colon tissue. to remove these nonspecific antibodies the rabbit antiserum was passed through Agarose gels, especially Sepharose affinity columns to which was bound proteins from the homogenized normal human colon tissue. This was repeated for removal of any activity against CEA antigens by passage through a CEA column. The effluent material was treated with a saturated ammonium sulphate $(NH_4)_2SO_4$ solution to precipitate the gamma globulins. This IgG fraction was radioiodinated with commercially available New England Nuclear $^{125}$I using lactoperoxidase according to the method of Heusser et al. described in Heusser, C. M., Boesman, J. H., Nordin and H. Isliker, Effect of chemical and enzymatic radioiodination on in vitro human Clq activities. J. Immunol. 110:820. (1973).

Purified Protein A from Staphlococcus Aureus Cowan strain, covalently coupled to CNBr-activated Agorese gels, especially Sepharose 4B, was used for the isolation of the in vivo formed soluble CIC. This suspension binds IC tenfold more rapidly than IgG alone. 500 lambda human serum samples were incubated with Protein A/Sepharose, washed, and the IC eluted with glycine/HCl and neutralized with NaOH. This preparation (Prep-IC) was ready for the assay or could be stored at 4° C. for one week.

One hundred lambda (100λ) glycine/HCl was added to 100λ Prep-IC and incubated. After this incubation 100λ of 125$_I$ labeled colon IgG was added and the final solution was neutralized. A 2.5% polyethylene glycol (PEG) 6000 solution in Borate Buffer pH 8.3 was used to precipitate the re-formed labeled IC which were then counted for radioactivity.

The results in Table 1 demonstrate (1) the importance of the novel methodology for the preparation of the products used to immunize an animal to make a specific antibody, (2) the importance of removing the soluble CIC from the patient's serum for the assay and (3) the dissociation of the IC into the antigen and antibody components before the addition of the radiolabeled antibody, (4) the neutralization of the solution to make re-formed immune complexes and (5) the counting of the re-formed IC to show if the patient has colon cancer.

TABLE 1

| Serum Sample | IC Removed | IC Dissociated | Assay Results Positive | Assay Results Negative |
|---|---|---|---|---|
| 1 Normal[1] | No | Yes | | X[3] |
| 2 Colon[2] | No | Yes | X | |
| 3 Normal | Yes | No | | X |
| 4 Colon | Yes | No | | X |
| 5 Normal | Yes | Yes | | X |

TABLE 1-continued

| Serum | IC | | Assay Results | |
|---|---|---|---|---|
| Sample | Removed | Dissociated | Positive | Negative |
| 6 Colon | Yes | Yes | X | |

[1] All normal samples from the same patient
[2] All colon samples from the same patient
[3] The mean of duplicate samples tested

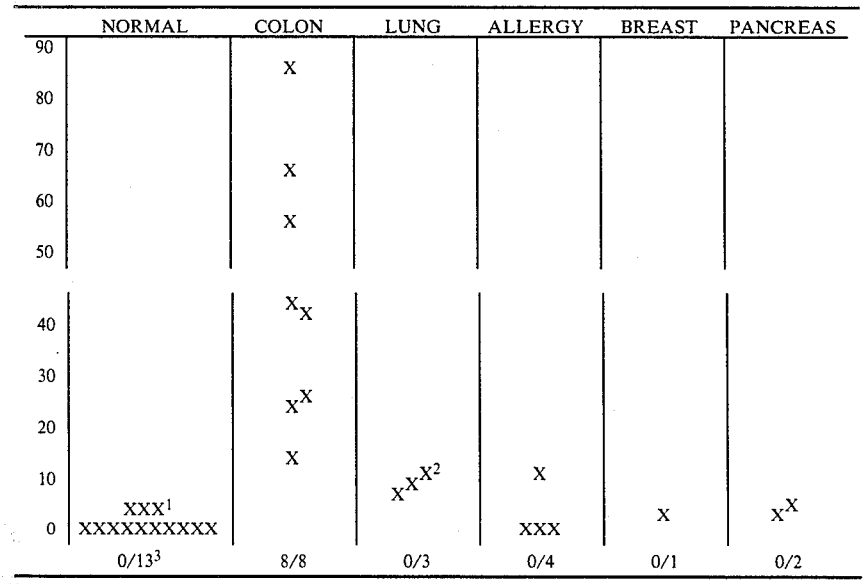

TABLE 2

|  | NORMAL | COLON | LUNG | ALLERGY | BREAST | PANCREAS |
|---|---|---|---|---|---|---|
| 90 |  | X |  |  |  |  |
| 80 |  |  |  |  |  |  |
| 70 |  | X |  |  |  |  |
| 60 |  | X |  |  |  |  |
| 50 |  |  |  |  |  |  |
| 40 |  | XX |  |  |  |  |
| 30 |  |  |  |  |  |  |
| 20 |  | XX |  |  |  |  |
| 10 |  | X | XXX[2] | X |  |  |
| 0 | XXX[1] XXXXXXXXXX |  |  | XXX | X | XX |
|  | 0/13[3] | 8/8 | 0/3 | 0/4 | 0/1 | 0/2 |

[1] Each X represents the average of a patient's serum sample that was assayed in duplicate.
[2] All values below 15 were considered normal.
[3] Positive for colon / Total number of tests As can be seen from the results in TABLE 2, samples from normals and patients with lung, breast and pancreas cancer and those with allergies were negative; whereas samples from patients with colon cancer were positive.

Consider now the principles of the invention. In the capillary culture system according to the invention an in vivo situation is simulated, where human colon tumor cells release shed antigens and by-products into the media for a period of approximately 2 weeks. In this system, due to the absence of antibody forming cells, no immune complexes are formed. However, immunizing a rabbit with the material in the media, might result in an antiserum similar to that produced in the patient with the original tumor. Because of species differences, the rabbit also produces antibodies directed against all the normal human antigens. Absorbtions with normal human colon tissues are necessary to remove these antibodies. The end result is a polyclonal antibody which is relatively specific for human colon tumor cells. Since tumor cells are heterogeneic, a polyclonal antibody would be an advantage in immune diagnosis because the sum total of the varied IC present in the serum of a patient with cancer would be very significant. However, a monoclonal antibody that would identify only one specific epitope might not show too great a difference from a normal and therefore would be considered negative. This is best demonstrated when treatment of tumors with chemotherapy achieves best results with a battery of drugs against the various tumor cells present. Based on these assumptions the labeled Igg fraction of rabbit antiserum becomes a very useful tool in the present assay according to the invention.

There are three important features of this protocol. First, the capillary culture system produces surface cell antigens and by-products that are not bound to any antibody. All the sites on these molecules are exposed to the rabbit when being immunized, thus resulting in an antiserum with more varied specificity. Second, removing the soluble CIC from the patient's serum allows dealing directly only with the complexes, without the possible inhibitive effect of other substances in the serum. Third, dissociation of the CIC into the initial antigen and antibody components before adding a labeled antibody is important. Since the radiolabeled antibody reacts positively with the dissociated antigen from CIC of the patient's serum, it indicates that there is a similarity between the antigen produced by the patient's tumor and the ECS of the cultured colon tumor cells.

Because of the low levels of soluble CIC in the serum of patients with early tumors, they might not be detected unless they were removed from the serum and dissociated for testing. If these procedures are not followed, an assay might give a negative instead of a positive result.

A suitable kit for testing serum samples for malignant cells may be provided. For example, a suitable kit for testing unknown serum samples for colon cancer may include the following items:

1. A simple monoclonal or pool of monoclonal antibodies produced either by hybridomas, or genetic engineering or any other method can be substituted in this protocol for our labeled polyclonal antibody.

2. If this protocol for testing unknown serum samples for colon cancer is sold as a kit, it would include the following items.

---

1-Two-1 ml suspensions of purified Protein A bound to CNBR activated Sepharose 4B in PBS.
2-.2 M glycine/HCl Buffer pH 2.8    50 mls/10X

|  | concentration |
|---|---|
| 3-PBS (phosphate buffered saline) pH 7.2 | 250 mls/10X |
| 4-BB (Borate buffer) pH 8.3 | 50 mls/10X |
| 5-PEG (polyethylene glycol)6000 | 100 gms |
| 6-polypropylene tubes 12 × 75 | 1000 |
| 7-125/ labeled anticolon cancer antibody | 1 ml High titre |
| 8-PBS/1% BSA | 125 mls |
| 9-PBS/1% BSA/.5% tween 20 | 100 mls |

Each unknown serum sample may be tested with a normal serum control and a PBS/1% BSA control. This exemplary kit may test up to 100 unknown serum samples.

While a specific protocol has been described, a simple monoclonal or pool of monoclonal antibodies produced either by hybridomas, or genetic engineering or any other method may be substituted in the specific protocol instead of our polyclonal antibody. Variations in the amounts of the items used in the assay may be substituted. Variations in incubation times may occur. A wide variety of tubes may be used, such as glass, polypropylene and other materials or conical centrifuge tubes.

There follows a comparison of a general protocol for practicing the invention setting forth in the left column specific steps in a successful procedure actually conducted while the right column contains some possible equivalent steps within the principles of the invention, these specific possible equivalents being by way of example only, and not intended to limit the invention.

GENERAL PROTOCOL

| ACTUAL TESTED PROCEDURES | POSSIBLE EQUIVALENT STEP |
|---|---|
| 1. Human colon tumor cells cultured in an Amicon capillary system | 1. Human colon tumors cultured in petri dishes or flasks etc. |
| 2. Immunize rabbit with byproducts of culture | 2. Immunize rabbit or any other animal with whole tumor cells or fragments of tumor cells |
| 3. Antibody produced in rabbit is labeled with 125/ by lactoperoxidase method | 3. Labeling of antibody can be done with any radioactive material or enzymes or fluorescent label etc. |
| 4. Blood samples drawn from patients or normals | 4. Same |
| 5. Process blood to produce serum | 5. Same |
| 6. Removal of immune complexes from serum with purified protein A from the staphlococcus Aureus Cowan strain | 6. Other methods for removing immune complexes C1q Binding Assay, Raji cell assay etc. |
| 7. Dissociate removed IC with .2 M glycine/HCl pH 2.8 | 7. Dissociate IC with MgCl₂ or any other chemical or method such as isoelectric focusing |
| 8. Combining our labeled antibody with the antigen component of the IC to produce re-formed IC | 8. Use UN labeled rabbit antibody to tumor associated antigen and followed by a second labeled anti rabbit antibody |
| 9. We use PEG 6000 to precipitate re-formed IC | 9. Protein A can also be used to precipitate IC |
| 10. reformed labeled IC are counted in a Packard gamma auto counter | 10. Any type counting equipment can be used |
| 11. Our tests are done in 12 × 75 conical centrifuge tubes | 11. Assays can be done in any tubes - flat bottom or conical centrifugal made from any material - and any size |
| 12. This assay is called a radioimmune assay - RIA | 12. When you use an enzyme to label antibody - assay is called EIA - Enzyme Immuno assay |

There has been described apparatus and techniques for enhancing early detection of human colon cancer, thereby enhancing the survival rate while reducing the physical impact of treatment on the patient. It is evident that those skilled in the art may now make numerous uses and modifications of and departures from the specific apparatus, materials and techniques described herein without departing from the inventive concepts. Consequently, the invention is to be construed as embracing each and every novel feature and novel combination of features present in or possessed by the apparatus, materials and techniques disclosed herein and limited solely by the spirit and scope of the appended claims.

What is claimed is:

1. An immunoassay method for the early detection of human colon cancer using a labeled antibody anti-human colon carcinoma which method includes the steps of, withdrawing blood from a patient to provide a blood sample, separating said blood sample into serum and packed red blood cells, removing immune complexes from said serum with protein A covalently bound to agarose gels, disassociating the removed immune complexes into antigen and antibody components with an aqueous solution of 2M glycine-Hcl pH 3.0, adding said labeled antibody to said antigen and antibody components to form a mixed solution containing said antigen and labeled and unlabeled antibody components, adding an aqueous solution of 1N NaOH pH 11.0 to said mixed solution to neutralize the mixed solution to pH 7.0 and re-form immune complexes in the neutralized mixed solution, precipitating said re-formed immune complexes with a solution of polyethylene glycol 6000 molecular weight, and detecting the precipitated re-formed immune complexes.

2. A method in accordance with claim 1 wherein said label is selected from the group consisting of fluorescent, enzyme and radio-isotope labels.

3. The method in accordance with claim 1 wherein said labeled antibody is produced by a method which includes the steps of, providing extra capillary samples from a capillary culture of viable human colon tumor cells, maintaining said capillary culture for a sufficient time to allow said human colon tumor cells to shed tumor antigens and cell byproducts, immunizing an animal with said extra capillary samples containing said shed tumor antigens and cell byproducts to produce antibodies, absorbing said antibodies with normal human colon antigens to produce specific anti-human colon cancer antibodies, and labeling said anti-human colon cancer antibodies.

* * * * *